United States Patent [19]

Mo

[11] Patent Number: 6,102,859
[45] Date of Patent: Aug. 15, 2000

[54] METHOD AND APPARATUS FOR AUTOMATIC TIME AND/OR LATERAL GAIN COMPENSATION IN B-MODE ULTRASOUND IMAGING

[75] Inventor: Larry Y. L. Mo, Waukesha, Wis.

[73] Assignee: General Electric Company, Milwaukee, Wis.

[21] Appl. No.: 09/203,440

[22] Filed: Dec. 1, 1998

[51] Int. Cl.[7] ..................................................... A61B 8/00
[52] U.S. Cl. ........................................... 600/443; 600/447
[58] Field of Search ..................................... 600/437, 440, 600/441, 443, 447; 73/625–628; 128/916

[56] References Cited

U.S. PATENT DOCUMENTS 5,477,858  12/1995  Norris ................................ 128/660.05

FOREIGN PATENT DOCUMENTS 0 867 147  9/1998  European Pat. Off. .
198 19 832  11/1998  Germany .
97/32277  9/1997  WIPO .

*Primary Examiner*—Marvin M. Lateef
*Assistant Examiner*—Ali M. Imam
*Attorney, Agent, or Firm*—Dennis M. Flaherty; Christian G. Cabou; Phyllis Y. Price

[57] ABSTRACT

A method and an apparatus for automating time-gain compensation (TGC) and lateral-gain compensation (LGC) based on the B-mode image data. The automatic gain adjustments are aimed at equalizing the mean signal intensities along the axial (for TGC) and/or lateral (for LGC) direction of the image, and suppressing any lateral band (for TGC) and/or sector (for LGC) that contains mostly noise. The automatic TGC/LGC adjustment method is implemented in software on a digital scanner and uses a noise model of the entire B-mode processing chain from the beamformer through the B-mode processor to the back-end video processor.

15 Claims, 3 Drawing Sheets

METHOD AND APPARATUS FOR AUTOMATIC TIME AND/OR LATERAL GAIN COMPENSATION IN B-MODE ULTRASOUND IMAGING

FIELD OF THE INVENTION

This invention generally relates to B-mode ultrasound imaging of biological tissues. In particular, the invention relates to methods for fine tuning a B-mode ultrasound image by adjusting the gain setting as a function of the axial and/or lateral position.

BACKGROUND OF THE INVENTION

In B-mode ultrasound imaging, two-dimensional images of tissue are created in which the brightness of a pixel is based on the intensity of the echo return. During conventional two-dimensional imaging, gain adjustments provide overall image changes. The gain is typically adjusted after beamforming and before signal processing, i.e., prior to envelope detection. Gain adjustment in the axial direction, known as "time gain compensation" (TGC), is carried out by increasing or decreasing gain as a function of depth. In addition, "lateral gain compensation" (LGC) can be used to adjust the gain setting as a function of lateral position.

The TGC block at the output of the beamformer is basically a depth-dependent gain control designed to compensate the received signal to correct for the attenuation caused by tissues at increasing depths. It is often set based on a nominal tissue attenuation factor (e.g., 0.5 dB/cm-MHz) and beam diffraction losses as a function of depth. The objective is to produce uniform tissue image brightness from the near field to the far field. In practice, the tissue attenuation properties may deviate from the assumed constant factor (or an application-dependent internal TGC curve), and may vary significantly with depth, especially if macroscopic structures and reflectors are present. Further, if the far-field regions are very noisy, it is desirable to suppress their pixel intensities for best overall image presentation. For these reasons, manual TGC adjustment is usually provided via a column of "slide pots" (potentiometers) or rotary knobs on the front panel, for different depth zones. The externally adjusted TGC for different depth zones is usually graphically displayed as a TGC curve in the monitor display. The TGC graphic is generated, for example, by a graphic processor as an overlay to the image display.

For cardiac sector imaging, the cardiac tissues/borders that run parallel to the ultrasound beam often do not produce strong echoes. Therefore, in addition to TGC, LGC adjustment has also proven useful for boosting cardiac borders within selected image sectors, while leaving the chambers dark. LGC allows the user to control gain in the lateral plane by adjusting the gain setting as a function of lateral position. For example, gain is controlled in small user-selected sectors across the image. LGC can be implemented at the same point as TGC in the B-mode processing path. A graph of the LGC curve similar to the TGC curve is also often displayed on the video monitor.

While state-of-the-art scanners provide the user with a host of selectable imaging parameters, including transmit frequency, acoustic output, external TGC and LGC controls, frame averaging level, dynamic range, edge-enhancing filters and video gray mapping, all of which can significantly affect the sensitivity, uniformity and feature enhancements of an image, the sonographer usually does not have the time (or training) to fully optimize all the available controls. To improve the ease-of-use and efficiency of the ultrasound examination, there is a need to automate some of the basic imaging parameter selection based on actual image data.

SUMMARY OF THE INVENTION

The present invention is a method for automating the external TGC and/or LGC adjustments based on the B-mode image data. The automatic gain adjustments are aimed at equalizing the mean signal intensities along the axial (for TGC) and/or lateral (for LGC) direction of the image, and suppressing any lateral band (for TGC) and/or sector (for LGC) that contains mostly noise. This automatic gain adjustment feature will reduce TGC or LGC adjustment time. Some additional manual adjustments (via the external TGC/LGC controls) can be made to further highlight edges or to fine tune the gain adjustments.

In accordance with the preferred embodiment, the automatic TGC/LGC adjustment method is implemented in software on a digital scanner. In practice, many variations in the basic system architecture are possible. In the preferred embodiment, the TGC/LGC functions are implemented between the beamformer and B-mode processor. In other system configurations, the TGC/LGC functions can be implemented in the analog front-end before the beamformer or after B-mode detection. In some conventional systems, the acoustic or R-θ data (before scan conversion) is stored in cine memory. The automatic TGC/LGC algorithm of the present invention can support all such standard architectural variations.

In accordance with the preferred embodiment of the invention, the automatic TGC/LGC adjustment method uses a noise model of the entire B-mode processing chain from the beamformer through the B-mode processor to the back-end video processor. Basically the noise model utilizes the fact that the primary noise source in a digital scanner lies in the front-end electronics (pre-amplifier), which can be modeled as white Gaussian noise whose RMS amplitude can be calibrated accurately (for normal operating temperature). Thus, by incorporating knowledge of the exact system bandwidths and gains at various points in the signal processing path, and of the display dynamic range setting and video gray mapping, the noise model can be used to predict the exact noise statistics (mean and probability distribution) in the B-mode image for any combination of internal (preset) TGC/LGC curve and front-panel gain settings.

In accordance with the preferred embodiments, an image frame of display pixel intensity values is divided into a regular grid of kernels by the host computer. The host computer then retrieves the current settings of all pertinent gain-related parameters for each kernel. A noise model is used to predict the mean noise level in each kernel. For each kernel, the host computer then calculates the mean (or total) pixel intensity and compares that to the predicted mean (or total) noise. [As used herein, the term "mean" means average.] Signal is deemed present in a kernel if its mean display pixel intensity is significantly above the predicted noise level. Otherwise the kernel is considered to contain only noise. For each row (sector), the kernels which contain signal are counted. If this number is less than a certain threshold, then that row (sector) is classified as "mostly noise". For each row (sector) whose signal kernel count is above the critical threshold, the host computer then computes the mean display pixel intensity, i.e., "row (sector) mean", of all kernels that contain signal (i.e. excluding kernels that do not contain signal). Based on a given optimal mean gray-scale level for the B-mode image display, the host computer then determines the gain adjustment for each row (sector) which will shift the gray-scale level (based on the current gray map settings) corresponding to the row (sector) mean to the optimal gray-scale level. The required gain adjustment can be computed in decibels using the noise model, which should take into account the current dynamic range and gray map settings. The gain adjustment is then applied to the raw acoustic data (RF or baseband) for each row (sector) to equalize the row (sector) means across the entire image.

Optionally, for the rows (sectors) which have been classified as "mostly noise," the row (sector) gain can be automatically reduced to suppress the noise.

In accordance with the preferred embodiments of the invention, either or both of the TGC and the LGC can be automated.

DETAILED DESCRIPTION OF THE PREFERRED EMBODIMENTS

Figure 1:
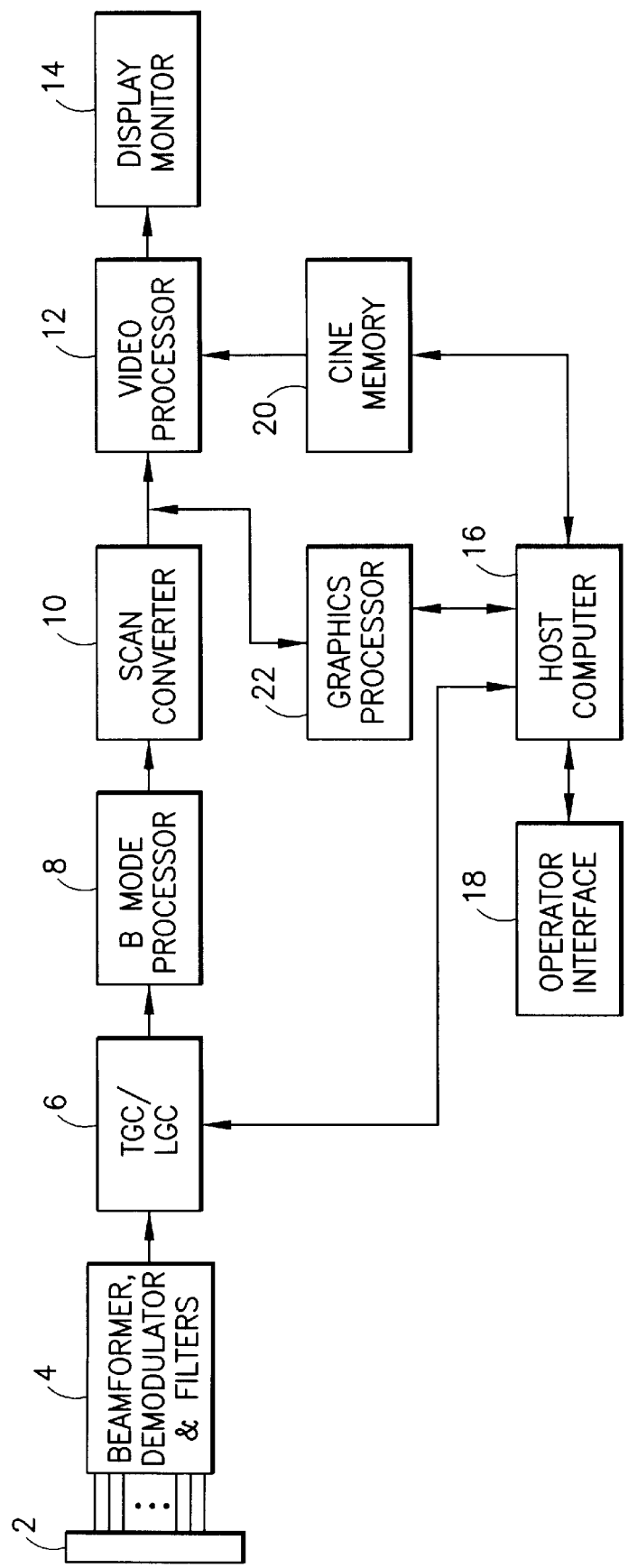
FIG. 1 is a schematic showing a block diagram of an ultrasound imaging system in accordance with the preferred embodiments of the invention.

An ultrasound imaging system in accordance with one preferred embodiment of the invention is generally depicted in FIG. 1. The main data path begins with the analog RF inputs to the beamformer board 4 from the transducer 2. The beamformer board 4 comprises a beamformer, a demodulator and filters. The beamformer's signal inputs are the low-level analog RF signals from the transducer elements. The beamformer is responsible for analog-to-digital conversion and for transmit and receive beamforming. The demodulator receives the acquired data samples and outputs two summed digital baseband I and Q receive beams. These acoustic data samples are derived from the reflected ultrasound from respective focal zones of the transmitted beams. The I and Q acoustic data from the demodulator is sent to respective FIR filters which are programmed with filter coefficients to pass a band of frequencies preferably centered at the fundamental frequency $f_0$ of the transmit waveform or a (sub)harmonic frequency thereof.

In accordance with the preferred embodiment of the invention, vectors of filtered I and Q acoustic data are input to a TGC/LGC block 6, which provides time gain and/or lateral gain compensation. Time gain compensation fine tunes the image in the axial direction by increasing or decreasing gain as a function of depth (time) for all received vectors. Lateral gain compensation fine tunes the image in the lateral direction by increasing or decreasing gain as a function of lateral position (beam or vector position). In the former case, gain is controlled in small rows of the image. In the latter case, gain is controlled in small sectors of the image.

Each I and Q vector input to TGC/LGC block 6 corresponds to a respective receive beam. For time gain compensation, block 6 applies depth-dependent digital gains to an acoustic data vector. For lateral gain compensation, block 6 applies angle-dependent digital gains to respective vectors of acoustic data. During scanning, successive vectors (A-lines) are input to TGC/LGC block 6 for gain compensation. In the case where both TGC and LGC are provided, a respective gain can be automatically applied to each point along a vector, the gain being a function of depth (i.e., range R) and vector angle (i.e., transmit beam angle θ).

The acoustic data output from the TGC/LGC block is sent to the B-mode processor 8. The B-mode processor 8 converts the I and Q acoustic data from TGC/LGC block 6 into a log-compressed version of the signal envelope. The B-mode function images the time-varying amplitude of the envelope of the signal as a gray scale. The envelope of a baseband signal is the magnitude of the vector which I and Q represent. The I,Q phase angle is not used in the B-mode display. The magnitude (i.e., intensity) of the signal is the square root of the sum of the squares of the orthogonal components, i.e., $(I^2+Q^2)^{1/2}$.

The B-mode intensity data is output to a scan converter 10 comprising a B-mode acoustic line memory followed by an X-Y display memory (not shown). The acoustic line memory accepts the processed vectors of B-mode intensity data and interpolates where necessary. The B-mode acoustic line memory also performs the coordinate transformation of the B-mode intensity data from polar coordinate (R-θ) sector format or Cartesian coordinate linear format to appropriately scaled Cartesian coordinate display pixel intensity data, which is stored in the X-Y display memory.

The scan-converted frames are passed to a video processor 12, which maps the pixel intensity data to a gray-scale mapping for video display. A conventional ultrasound imaging system typically employs a variety of gray maps, which are simple transfer functions of the raw intensity data to display gray-scale levels. The gray-scale image frames are then sent to the display monitor 14 for display.

The B-mode images displayed by monitor 14 are produced from an image frame of data in which each datum indicates the intensity or brightness of a respective pixel in the display. An image frame may, e.g., comprise a 256×256 data array in which each display pixel intensity datum is an 8-bit binary number that indicates pixel brightness. Each pixel has an intensity value which is a function of the backscatter cross section of a respective sample volume in response to interrogating ultrasonic pulses and the gray map employed. The displayed image represents the tissue and/or blood flow in a plane through the body being imaged.

Successive frames of display pixel intensity data are stored in a cine memory 20 on a first-in, first-out basis. The cine memory stores the pixel intensity data which has already been combined with the TGC and all other graphic data. The cine memory also stores the pixel intensity data which is already converted in the first portion of the video processor into video frame rate, but before gray mapping. Storage can be continuous or as a result of an external trigger event. The cine memory 20 is like a circular image buffer that runs in the background, capturing image data that is displayed in real time to the user. When the user freezes the system (by operation of an appropriate device on the operator interface 18), the user has the capability to view image data previously captured in cine memory.

System control is centered in a host computer 16, which accepts operator inputs through the operator interface 18 (e.g., a control panel) and in turn controls the various subsystems. The host computer 16 performs system level control functions. A system control bus (not shown) provides the interface from the host computer to the subsystems. A scan controller (not shown) provides real-time (acoustic vector rate) control inputs to the various subsystems. The scan controller is programmed by the host computer with the vector sequences and synchronization options for acoustic frame acquisitions. Thus, the scan controller controls the beam distribution and the beam density. The scan controller transmits the beam parameters defined by the host computer to the subsystems via a scan control bus (not shown).

The conventional system has the capability to superimpose graphical symbols on any ultrasound image. The superimposition of graphics on the image frame is accomplished in the video processor 12, which receives the ultrasound image frame from the X-Y display memory in the scan converter 10 and the graphics data from a graphics display memory (not shown). The graphics data is processed and input into the graphics display memory by a graphics processor 22 which is synchronized with the other subsystems by the host computer.

The automated TGC/LGC adjustment method can be implemented in software by the host computer. One key component of the method is a noise model of the entire B-mode processing chain from the beamformer through the B-mode processor to the back-end video processor. For a given position (x, y) in the B-mode image frame, the image noise model is used to predict the noise level (as a B-mode intensity or gray-scale level) at that position. For contemporary digital scanners, the image noise model consists of several key components, the details of which depend on the specific subsystem design for a particular scanner. The noise/gain calculations involved in each component are standard practices in systems design, so only the main function of each component are described in the following.

Figure 2:
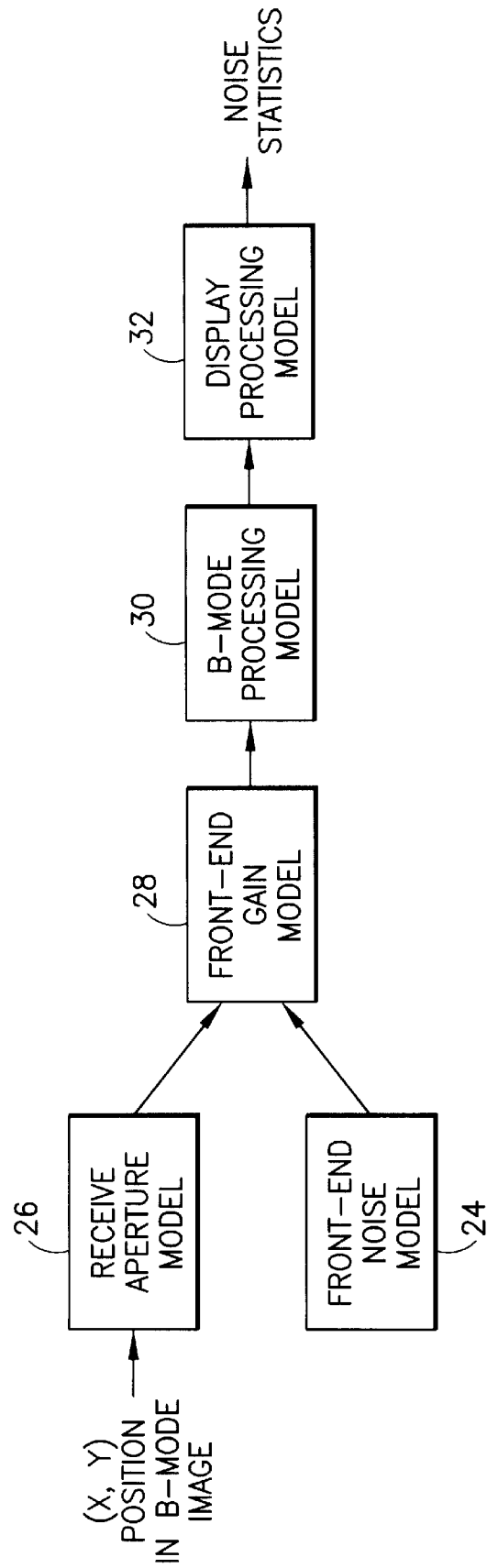
FIG. 2 is a schematic showing a block diagram of a B-mode image noise model used in performing the TGC and LGC in accordance with the preferred embodiments of the invention.

A B-mode image noise model suitable for use in the preferred embodiment of the invention is generally depicted in FIG. 2. The front-end noise model (block 24) computes the Gaussian noise level generated by the front-end electronics (e.g., the pre-amplifier) in a single receive channel and any quantization noise associated with analog-to-digital conversion. The analog electronics noise is often referred to as thermal noise and can be calibrated accurately for a given temperature range. Depending on the electrical impedance of the transducer which is connected to the front end, the thermal noise may or may not have a flat spectral power density.

The number of receive channels contributing noise is dependent on the receive aperture size, which is computed by the receive aperture model (block 26) based on the known aperture control parameters (i.e., F number and shading) for the given probe and (x, y) position.

The front-end gain model (block 28) computes the total noise from all independent receive channels, and incorporates the effects of all filtering gains in the beamformer, including any TGC/LGC.

The B-mode processing model (block 30) adjusts the noise for the noise gains that occur in the B-mode detector and filters including scan conversion. Standard noise theory indicates that the detected envelope of Gaussian noise obeys the Rayleigh probability distribution, which is completely specified by its mean.

The display processing model (block 32) accounts for the effects of logarithmic compression and gray mapping, and outputs the predicted noise distribution at the inputted (x, y) position in the image.

The above-described noise model is run by the host computer. Prior to running the noise model, the host computer needs to read out all pertinent internal and external system settings, such as the current TGC curve, transmit focal zone positions, image depth, display dynamic range setting and gray mapping setting. The host computer then feeds these parameters into the various components of the image noise model.

The host computer also performs the automatic TGC/LGC algorithm. It is assumed that an image of the region of interest is currently displayed on the video monitor. The automatic TGC/LGC can be activated via a single button (or soft-key). The main steps in the TGC/LGC algorithm in accordance with one preferred embodiment are outlined as follows.

Figure 3:
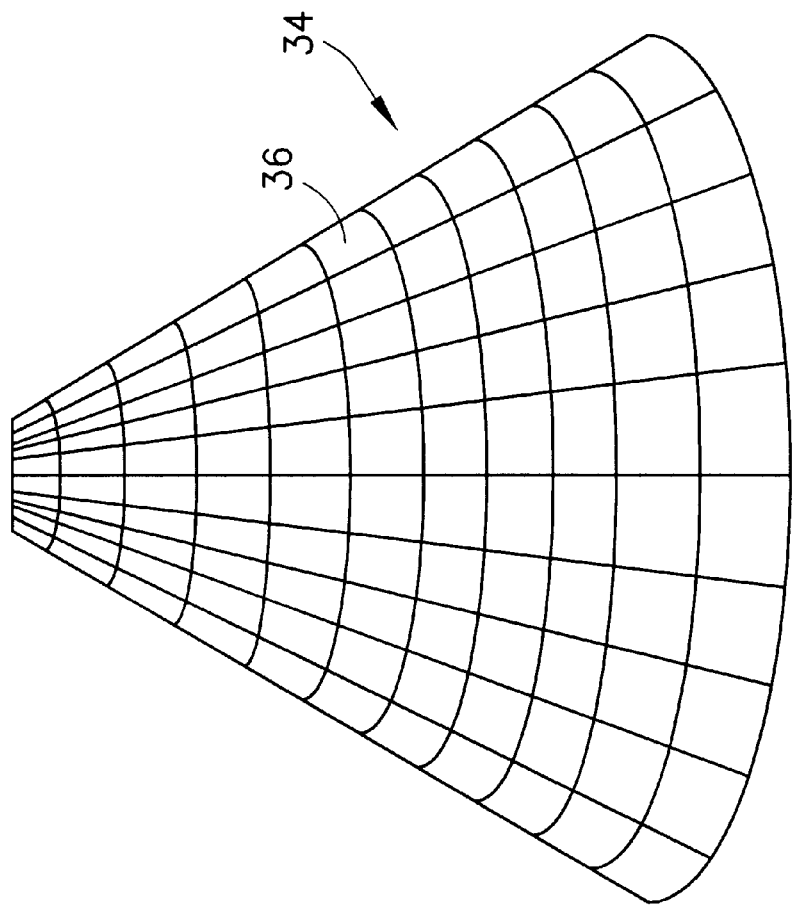
FIG. 3 is a schematic depicting an ultrasound sector image which has been divided into a regular grid of kernels for use in TGC and LGC.

In response to activation of the automatic TGC/LGC function, the image is frozen momentarily to allow one to several most recent image frames to be saved to cine memory, which can then be read out by the host computer for analysis. If more than one is used, a mean is taken to reduce statistical variations before image analysis. The size of the image (single or mean) is determined, and is then divided into a regular grid 34 of kernels 36 as shown in FIG. 3, where the number of rows and sectors (columns) of kernels in the grid should be at least as large as the number of the respective TGC and LGC knobs/slide pots on the front panel. The kernel dimensions are defined by equal range and vector angle spacings for a sector or curvilinear scan (as shown in FIG. 3), and they are rectangles or squares for a linear scan.

The host computer retrieves the current settings of all pertinent gain-related parameters, such as internal TGC, receive aperture and B-mode processor gains, for each kernel within the grid. These can usually be read out from other system programs or computed from known system parameters. These parameter values are input to the noise model to predict the mean noise level in each kernel of the grid.

For each kernel in the grid the host computer compares the mean (or total) pixel intensity to the predicted mean (or total) noise. Signal is present if the mean pixel intensity of a kernel is significantly (e.g., 10 dB) above the predicted mean noise level for that same kernel. Otherwise the kernel is considered to contain noise only.

For automatic TGC compensation, the following steps are performed. For each row, the kernels which contain signal are counted. If this number is less than a certain threshold (e.g., 10% of the total number of kernels in a row), then that row is classified as "mostly noise." For each row whose signal kernel count is above the critical threshold, the mean pixel intensity of all kernels that contain signal (i.e. excluding kernels that do not contain signal) is computed. This gives the "row mean", which can be converted to a gray-scale level by the host computer referring to the current gray mapping settings. Based on a given optimal mean gray-scale level for the B-mode image display (e.g., for an 8-bit video gray scale, the optimal mean gray-scale level may be 200), the host computer then determines the gain adjustment for each row which will shift the row mean gray-scale level to the optimal gray-scale level. The gain adjustment required can be computed using the noise model, which should take into account the current dynamic range and gray map settings. In fact, it should be exactly equivalent to adjusting the external TGC knobs, which may affect the front-end and/or B-mode processor gains depending on the system architecture. In the preferred embodiment, the gain adjustments for each row are applied in block 6 (see FIG. 1) to equalize the row means across the entire image. This is effected exactly as if the user were applying the same gain adjustments via the front-panel TGC slide pots or knobs. Optionally, for the rows which have been classified as "mostly noise," the row gain can be automatically turned down to suppress the noise (by shifting down its mean gray-scale level by a fixed amount or shifting it down towards zero grayscale level).

For automatic LGC, the procedure is exactly parallel to that for automatic TGC described above. For each sector (for sector scans) or column (for linear scans), the kernels which contain signal are counted. If this number is less than a certain threshold (e.g., 10% of the total number of kernels in a sector or column), then that sector (column) is classified as "mostly noise." For each sector (column) whose signal kernel count is above the critical threshold, the mean pixel intensity of all kernels that contain signal (i.e., excluding kernels that do not contain signal) is computed. This gives the "sector (column) mean", which can be converted to a gray-scale level by the host computer referring to the current gray mapping settings. Based on the optimal mean gray-scale level previously described, the host computer then determines the gain adjustment for each sector (column) which will shift the sector (column) mean gray-scale level to the optimal grayscale level. Again the required gain adjustment is computed using the noise model, taking into account the current dynamic range and gray map settings. Again, this should be exactly equivalent to adjusting the external LGC knobs. The gain adjustments for each sector (column) are applied in block 6 (see FIG. 1) to equalize the sector (column) means across the entire image. Again, for those sectors (columns) which have been classified as "mostly noise," the sector (column) gain can be automatically turned down to suppress the noise.

The graphics processor 22 (see FIG. 1) supplies graphic data to the video processor 12 for display on the monitor 14. This graphic data is designed to indicate the magnitudes of the automatic gain adjustments and the corresponding relative positions in the image. Preferably, the graphic data take the form of TGC and LGC curves. The TGC curve and LGC curve graphics in the display monitor are updated automatically by the graphics processor. A different line-type can be used to display the automatic TGC and LGC curves so they can be distinguished from the curves corresponding to the TGC and LGC slide pot positions. For example, if automatic TGC is activated, a solid curve can be used to display the active TGC curve and a dashed line for the manually set TGC curve. If automatic TGC is turned off, the dashed curve reverts back to a solid curve to indicate that the slide-pot TGC curve is now active again.

In accordance with the preferred embodiment, automatic TGC and LGC are both applied by the host computer to control gain in the lateral and axial planes. Alternatively, the host may apply only one or the other type of gain compensation.

The foregoing preferred embodiments have been disclosed for the purpose of illustration. Variations and modifications of the concept of the invention will be readily apparent to persons skilled in the art. For example, the automated TGC/LGC functions of the invention are not limited to being implemented between the beamformer and B-mode processor, but instead can be implemented in the analog front-end before the beamformer or after B-mode detection. Moreover, the invention is not limited to processing of display intensity data. For systems in which the acoustic or R-θ data (before scan conversion) is stored in cine memory, the automatic TGC/LGC algorithm can be applied to the raw acoustic data instead of the display intensity data. All such variations and modifications are intended to be encompassed by the claims set forth hereinafter.

As used in the claims, the term "acoustic data" refers to the received signal at any point between the transducer and the scan converter; the term "pixel intensity data" refers to the scan-converted signals prior to gray mapping; and the term "gray-scale level data" refers to the gray-mapped pixel intensity data output to the display device. The term "kernel having signal", as used in the claims, means a kernel having a mean pixel intensity which is greater than the predicted mean noise level for that same kernel by a predetermined quantity. It will also be appreciated that calculation of the total pixel intensity value within a kernel is the equivalent of calculation of the mean pixel intensity, as recited in the claims.

What is claimed is:

1. A system for imaging biological tissues, comprising:

an ultrasound transducer array comprising a multiplicity of transducer elements;

a transmit beamformer for pulsing said transducer array to transmit ultrasound beams in first and second scans;

a receive beamformer for forming receive beams of acoustic data derived from echo signals detected by the transducer array subsequent to said transmissions;

a signal processing chain for converting said acoustic data into first and second image frames of pixel intensity data corresponding to said first and second scans respectively, said signal processing chain comprising a gain compensation component for adjusting the gain of the acoustic data as a function of gain adjustments;

a computer programmed to determine said gain adjustments as a function of said first image frame of pixel intensity data and the current settings of all pertinent gain-related system parameters in accordance with a noise model, and transmit said gain adjustments to said gain compensation component in time to adjust the gain of the acoustic data acquired from said second scan;

a video processor for converting said image frame of pixel intensity data into an image frame of gray-scale level data; and a display device for displaying an image representing said image frame of gray-scale level data, wherein said computer is programmed to perform the following steps:

(a) dividing said first image frame of pixel intensity data into a regular grid of kernels forming a plurality of rows;

(b) retrieving the current settings of all pertinent gain-related parameters for each kernel;

(c) predicting the mean noise level in each kernel using said noise model;

(d) calculating the mean pixel intensity for each kernel;

(e) comparing the predicted mean noise level with the calculated mean pixel intensity for each kernel;

(f) for each row satisfying a predetermined condition, determining a mean pixel intensity of all kernels having signal to form a row mean;

(g) based on an optimal mean gray-scale level, determining the gain adjustment for each row which will shift the gray-scale level corresponding to the respective row mean to said optimal gray-scale level; and (h) sending said gain adjustments to said gain compensation component.

2. The system as recited in claim 1, wherein said computer is further programmed to determine the respective downward gain adjustment which will suppress the noise for each row whose count of kernels having signal is less than said critical threshold.

3. A system for imaging biological tissues, comprising:
an ultrasound transducer array comprising a multiplicity of transducer elements;
a transmit beamformer for pulsing said transducer array to transmit ultrasound beams in first and second scans;
a receive beamformer for forming receive beams of acoustic data derived from echo signals detected by the transducer array subsequent to said transmissions;
a signal processing chain for converting said acoustic data into first and second image frames of pixel intensity data corresponding to said first and second scans respectively, said signal processing chain comprising a gain compensation component for adjusting the gain of the acoustic data as a function of gain adjustments;
a computer programmed to determine said gain adjustments as a function of said first image frame of pixel intensity data and the current settings of all pertinent gain-related system parameters in accordance with a noise model, and transmit said gain adjustments to said gain compensation component in time to adjust the gain of the acoustic data acquired from said second scan;
a video processor for converting said image frame of pixel intensity data into an image frame of gray-scale level data; and
a display device for displaying an image representing said image frame of gray-scale level data, wherein said computer is programmed to perform the following steps:
(a) dividing said first image frame of pixel intensity data into a regular grid of kernels forming a plurality of sectors;
(b) retrieving the current settings of all pertinent gain-related parameters for each kernel;
(c) predicting the mean noise level in each kernel using said noise model;
(d) calculating the mean pixel intensity for each kernel;
(e) comparing the predicted mean noise level with the calculated mean pixel intensity for each kernel;
(f) for each sector satisfying a predetermined condition, determining a mean pixel intensity of all kernels having signal to form a sector mean;
(g) based on an optimal mean gray-scale level, determining the gain adjustment for each sector which will shift the grayscale level corresponding to the respective sector mean to said optimal gray-scale level; and
(h) sending said gain adjustments to said gain compensation component.

4. The system as recited in claim 3, wherein said computer is further programmed to determine the respective downward gain adjustment which will suppress the noise for each sector whose count of kernels having signal is less than a critical threshold.

5. A system for imaging biological tissues, comprising:
an ultrasound transducer array comprising a multiplicity of transducer elements;
a transmit beamformer for pulsing said transducer array to transmit ultrasound beams in first and second scans;
a receive beamformer for forming receive beams of acoustic data derived from echo signals detected by the transducer array subsequent to said transmissions;
a signal processing chain for converting said acoustic data into first and second image frames of pixel intensity data corresponding to said first and second scans respectively, said signal processing chain comprising a gain compensation component for adjusting the gain of the acoustic data as a function of gain adjustments;
a computer programmed to determine said gain adjustments as a function of said first image frame of pixel intensity data and the current settings of all pertinent gain-related system parameters in accordance with a noise model, and transmit said gain adjustments to said gain compensation component in time to adjust the gain of the acoustic data acquired from said second scan;
a video processor for converting said image frame of pixel intensity data into an image frame of gray-scale level data; and
a display device for displaying an image representing said image frame of gray-scale level data, wherein said computer is programmed to perform the following steps:
(a) dividing said first image frame of pixel intensity data into a regular grid of kernels having a plurality of columns;
(b) retrieving the current settings of all pertinent gain-related parameters for each kernel;
(c) predicting the mean noise level in each kernel using said noise model;
(d) calculating the mean pixel intensity for each kernel;
(e) comparing the predicted mean noise level with the calculated mean pixel intensity for each kernel;
(f) for each column satisfying a predetermined condition, determining a mean pixel intensity of all kernels having signal to form a column mean;
(g) based on an optimal mean gray-scale level, determining the gain adjustment for each column which will shift the grayscale level corresponding to the respective column mean to said optimal gray-scale level; and
(h) sending the gain adjustments to said gain compensation component.

6. The system as recited in claim 5, wherein said computer is further programmed to determine the respective downward gain adjustment which will suppress the noise for each column whose count of kernels having signal is less than a critical threshold.

7. A method for automatically adjusting gain in an ultrasound imaging system, comprising the steps of:
(a) dividing an image frame of pixel intensity data into a regular grid of kernels forming a plurality of sets of aligned kernels;
(b) retrieving the current settings in said ultrasound imaging system of all pertinent gain-related parameters for each kernel;
(c) predicting the mean noise level in each kernel using a noise model;
(d) calculating a function of the pixel intensity for each kernel;
(e) comparing the predicted mean noise level with the calculated pixel intensity function for each kernel;
(f) for each kernel set satisfying a predetermined condition, determining a mean pixel intensity of all kernels having signal to form a kernel set mean;
(g) based on an optimal mean gray-scale level, determining the gain adjustment for each kernel set which will shift the gray-scale level corresponding to the respective kernel set mean to said optimal gray-scale level; and (h) adjusting the gain in accordance with said gain adjustments during subsequent operation of said ultrasound imaging system.

8. The method as recited in claim 7, wherein said function is mean pixel intensity.

9. The method as recited in claim 7, wherein said function is total pixel intensity.

10. The method as recited in claim 7, wherein each kernel set forms a respective row in said grid.

11. The method as recited in claim 7, wherein each kernel set forms a respective sector in said grid.

12. The method as recited in claim 7, wherein each kernel set forms a respective column in said grid.

13. The method as recited in claim 7, wherein said gain adjustments are varied along each vector of acoustic data.

14. The method as recited in claim 7, wherein said gain adjustments are varied across vectors of acoustic data.

15. The method as recited in claim 7, further comprising the step of determining a respective down-ward gain adjustment which will suppress the noise for each kernel set whose count of kernels having signal is less than a critical threshold.

* * * * *